United States Patent [19]

Kume et al.

[11] Patent Number: 4,836,844
[45] Date of Patent: Jun. 6, 1989

[54] NOVEL N-BENZOTHIAZOLYL-2,5-DIHYDROPYR-ROLES

[75] Inventors: Toyohiko Kume, Hino; Toshio Goto, Machida; Atsumi Kamochi, Hino; Akihiko Yanagi, Oume; Hidenori Hayakawa, Sagamihara; Shigeki Yagi, Tokyo, all of Japan

[73] Assignee: Nihon Tokushu Noyaku Seizo K.K., Tokyo, Japan

[21] Appl. No.: 66,914

[22] Filed: Jun. 25, 1987

[30] Foreign Application Priority Data

Jul. 9, 1986 [JP] Japan .................. 61-159595

[51] Int. Cl.$^4$ .................. C07D 417/02; A01N 43/78
[52] U.S. Cl. .......................... 71/90; 548/162
[58] Field of Search .................. 548/162; 71/90

[56] References Cited

U.S. PATENT DOCUMENTS 3,833,619 9/1974 Baumann .................. 548/162
4,220,655 9/1980 Böhner et al. .................. 549/551

FOREIGN PATENT DOCUMENTS 032879 7/1981 European Pat. Off. .................. 71/90
2450257 9/1980 France .................. 71/90

*Primary Examiner*—Robert Gerstl
*Attorney, Agent, or Firm*—Sprung Horn Kramer & Woods

[57] ABSTRACT

Novel herbicidally active N-benzothiazolyl-2-5-dihydropyrroles of the formula

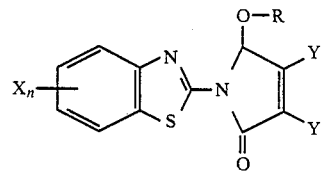

in which
R is hydrogen or an acyl group,
X is a halogen atom, an alkyl group, a haloalkyl group, a haloalkoxy group or a phenyl group,
n is 0, 1 or 2, and
Y is an alkyl group.

11 Claims, No Drawings

NOVEL N-BENZOTHIAZOLYL-2,5-DIHYDROPYRROLES

The present invention relates to novel N-benzothiazolyl-2,5-dihydropyrroles, to processes for their preparation and to their use as herbicides.

It has already been disclosed that certain 3,4-dimethyl-2-hydroxy-5-oxo-2,5-dihydropyrrole derivatives have herbicidal activities. (See U.S. Pat. Nos. 4,138,243 and 4,220,655)

There have now been found novel N-benzothiazolyl-2,5-dihydropyrroles of the formula (I)

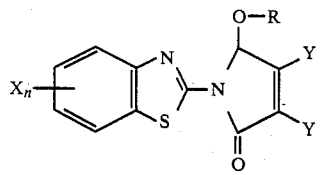

In the formula, R represents a hydrogen atom or an acyl group, X represents a halogen atom, an alkyl group, a haloalkyl group, a haloalkoxy group or a phenyl group, n represents 0, 1 or 2, and Y represents an alkyl group.

The compounds of the formula (I) are obtained by a process in which,
(a) in the case where R is a hydrogen atom: compounds of the formula (II)

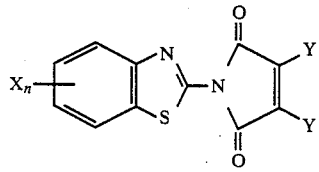

wherein X, n and Y are as defined, are reacted with a reducing agent, in the presence of inert solvents, or
(b) in the case where R is an acyl group:

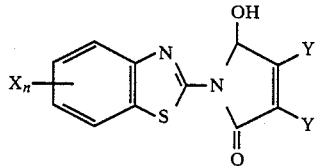

wherein X, n and Y are as defined, are reacted with compounds of the formula (III)

R'—Hal (III)

wherein R' is an acyl group, and Hal represents a halogen atom, or compounds of the formula (IV)

R'—O—R' (IV)

wherein R' is as defined, in the presence of inert solvents, and if appropriate in the presence of acid binders.

The novel N-benzothiazolyl-2,5-dihydropyrroles exhibit powerful herbicidal properties.

Surprisingly, the N-benzothiazolyl-2,5-dihydropyrroles according to the invention exhibit not only a substantially greater herbicidal action than those known from aforesaid prior art, but also a favorable compatibility with crops, without phytotoxicity.

Preferably, in the compounds of this invention represented by the formula (I), R represents a hydrogen atom or an acetyl group, X represents a fluorine atom, a chlorine atom, a bromine atom, an alkyl group having 1 to 3 carbon atoms, a fluoro-substituted alkyl group having 1 to 3 carbon atoms, a fluorosubstituted alkoxy group having 1 to 3 carbon atoms or a phenyl group, n represents 0, 1 or 2, and Y represents a methyl or ethyl group.

Expecially preferably, in the formula (I), R represents a hydrogen atom, X represents a fluorine atom, a chlorine atom, methyl, ethyl, n-propyl or isopropyl group, a trifluoromethyl group or a difluoromethoxy, trifluoromethoxy or tetrafluoroethoxy group, n represents 0, 1 or 2 and Y represents a methyl or ethyl group.

Specific examples of the compounds of the formula (I) include

N-(2-benzothiazolyl)-3,4-dimethyl-2-hydroxy-5-oxo-2,5-dihydropyrrole,

N-(6-fluoro-2-benzothiazolyl)-3,4-dimethyl-2-hydroxy-5-oxo-2,5-dihydropyrrole,

N-(6-trifluoromethoxy-2-benzothiazolyl)-3,4-dimethyl-2-hydroxy-5-oxo-2,5-dihydropyrrole, N-(5-trifluoromethyl-2-benzothiazolyl)-3,4-dimethyl-2-hydroxy-5-oxo-2,5-dihydropyrrole, and N-(6-isopropyl-2-benzothiazolyl)-3,4-dimethyl-2-hydroxy-5-oxo-2,5-dihydropyrrole.

When in process (a), N-(2-benzothiazolyl)-2,3-dimethylmaleimide and sodium borohydride, for example, are used as starting materials, the reaction is shown by the following reaction scheme.

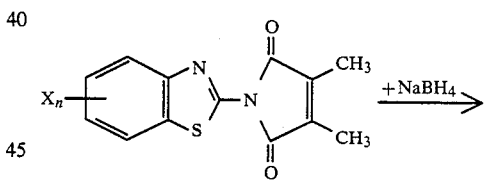

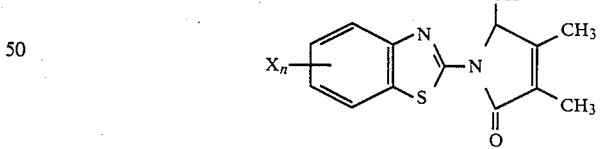

When in process b) N-(6-fluoro-2-benzothiazolyl)-3,4-dimethyl-2-hydroxy-5-oxo-2,5-dihydropyrrole and acetyl chloride, for example, are used as starting material, the reaction is shown by the following scheme.

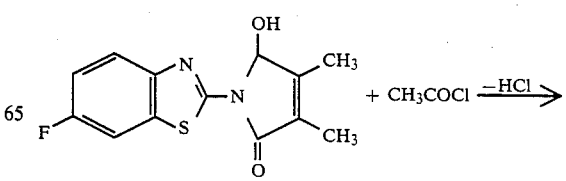

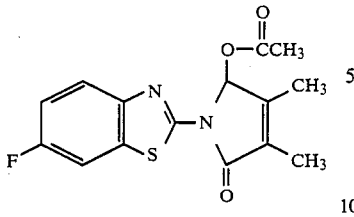

In process (a), the starting compound of formula (III) means one based on the definitions of X, n and Y, preferably the preferred definitions given above.

The compounds of the formula (II) are novel compounds, and can be obtained, for example, by reacting compounds of the formula (V)

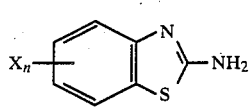

wherein X and n are as defined above, with compounds of the formula (VI)

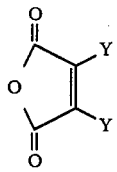

wherein Y is as defined above, or with 2 moles, per mole of the compounds of the formula (V), of maleic anhydride.

The compounds of the formula (V) include novel and known compounds.

The compounds of the formula (V) can be obtained, for example, by cyclizing anilines of the formula (VII)

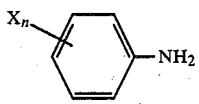

wherein X and n are as defined above, using bromine and thiocyanate in accordance with the method described in French Pat. No. 1,502,178; or by oxidatively cyclizing thioureas of the formula (VIII)

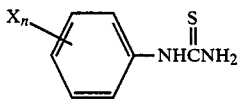

wherein X and n are as defined above, in accordance with the method described in Org. Synthesis, Vol. 22, pages 16-19 and Japanese Laid-Open Patent Publication No. 59679/1984; or by reacting compounds of the formula (IX)

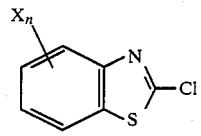

with ammonia in accordance with the method of "Yakugaku Zasshi", Vol. 78, pages 437-438.

The compounds of the formula (VII) are well known in the field of organic chemistry, and the compounds of the formula (VIII) can be easily obtained by reacting the anilines of the formula (VII) with isothiocyanic acid. The compounds of the formula (IX) are known compounds described, for example, in Japanese Patent Laid-Open No. 70678/1984 or European Laid-Open Patent Publication No. 43573.

The compounds of the formula (VI) in process (a) are described in Japanese Patent Laid-Open No. 23965/1978, and a typical example is 2,3-dimethylmaleic anhydride.

2,3-Disubstituted maleic anhydride other than the 2,3-dimethylmaleic anhydride, for example 2,3-diethylmaleic anhydride, can be obtained by following the methods described in Journal of the Japanese Chemical Society, Vol. 9, pages 1291-1293, 1983 and Summary of Papers Read in the 50th Annular Meeting of the Japanese Chemical Society, Vol. II, page 825, 1986. Alternatively, it may be obtained by hydrolyzing diethyl 2,3-diethylmaleate described in Synthetic Communications, Vol. 14, No. 13, pages 1193-1198, 1984 in a customary manner, and reacting the product with acetyl chloride. In addition, 2,3-disubstituted maleic anhydrides can also be produced by the method described in Journal of Organic Chemistry, Vol. 38, pages 3386-3389, 1973.

Specific examples of the compounds of the formula (II) include

N-(2-benzothiazolyl)-dimethylmaleimide,
N-(6-fluoro-2-benzothiazolyl)-dimethylmaleimide,
N-(6-trifluoromethoxy-2-benzothiazolyl)-dimethylmaleimide, and
N-(5-trifluoromethyl-2-benzothiazolyl)-dimethylmaleimide.

Examples of the reducing agent used in process (a) are metal hydrides such as sodium borohydride and lithium aluminum hydride.

The compounds of formula (I-a) used as starting materials in process (b) are included within the compounds of formula (I) provided by this invention which can be produced by process (a).

The compounds of formula (III) or (IV) which are likewise starting materials mean one based on the above definitions of R' and Hal, preferably those in which R' is an acetyl group and Hal is a chlorine atom.

Acetyl chloride cited as a specific example of the compounds of the formula (III) is well known. The compounds of the formula (IV) are also well known, and acetic anhydride can be cited as a specific example.

In the practice of process (a), all inert organic solvents may be used as suitable diluents.

Examples of the diluents are water, ethers (such as dioxane and tetrahydrofuran), alcohols (such as methanol, ethanol, isopropanol, butanol and ethylene glycol), and acid amides (such as dimethylformamide).

Process a) can be practiced within a substantially broad temperature range, for example at a temperature between about −20° C. and about 80° C., preferably between about 0° C. and about 30° C.

Desirably, the reaction is carried out under atmospheric pressure, but it is also possible to operate under elevated or reduced pressure.

In the practice of process (a), the desired compound of formula (I) can be easily obtained by reducing the compound of formula (II) with the above-exemplified reducing agent as shown in the examples hereinbelow.

In the practice of process (b), ethers (such as dioxane and tetrahydrofuran), acid amides (such as dimethylformamide, dimethylacetamide and hexamethylphosphoric triamide) and sulfoxides (such as dimethyl sulfoxide) may be cited as examples of suitable diluents.

Process (b) may be carried out in the presence of an acid binder. Examples of the acid binder are hydrides, hydroxides, carbonates, bicarbonates and alcoholates of alkali metals, and tertiary amines such as triethylamine, diethylaniline, pyridine and 4-dimethylaminopyridine.

Process (b) can be practiced over a substantially broad temperature range, for example at a temperature between about 50° C. and about 200° C., preferably between about 80° C. and about 160° C.

Desirably, the reaction is carried out under atmospheric pressure, but it is also possible to operate at elevated or reduced pressure.

In the practice of process (b), the desired compounds of the formula (I) can be obtained by reacting 1 mole of the compounds of the formula (I-a) with 1 to about 1.5 moles of the compounds of the formula (III) or (IV) in an inert solvent, if desired in the presence of an acid binder.

The active compounds according to the invention can be used as defoliants, desiccants, agents for destroying broad-leaved palnts and, especially, as weedkillers. By weeds, in the broadest sense, there are to be understood all plants which grow in locations where they are undesired. Whether the substances according to the invention act as total or selective herbicides depends essentially on the amount used.

The active compouns according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicom, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be emplyed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the slective combating of weeds in annual cultures.

The active compounds can be converted into the customary formulations, such as solutions, emulsions, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixes being possible.

Mixtures with other known active compounds, such as herbicides, fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing. They are used, in particular, after emergence of the plants.

The amount of active compound used can vary within a substantial range. It depends essentially on the nature of the desired effect. In general, the amounts used are between about 0.05 and about 5 kg of active compound per hectare of soil surface, preferably between about 0.1 and about 2.5 kg per ha.

The preparation and use of the active compounds according to the invention can be seen from the following examples.

Production Examples:

EXAMPLE 1

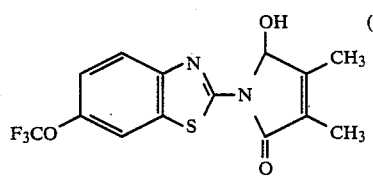
(compound No. 4)

N-(6-trifluoromethoxy-2-benzothiazolyl)-dimethylmaleimide (3.42 g) was added to methanol (150 ml), and sodium borohydride (0.19 g) was added at room temperature over 15 minutes. The mixture was further stirred for 3 hours. After the reaction, the reaction mixture was neutralized with acetic acid, and methanol was evaporated under reduced pressure. The residue was mixed with water and extracted with chloroform. Chloroform extracts were combined, and dried over anhydrous magnesium sulfate, and the solvent was evaporated under reduced pressure. The solid residue was washed with a small amount of diethyl ether to give the desired N-(6-trifluoromethoxy-2-benzothiazolyl)-3,4-dimethyl-2-hydroxy-5-oxo-2,5-dihydropyrrole (3.05 g). m.p. 228°–231° C.

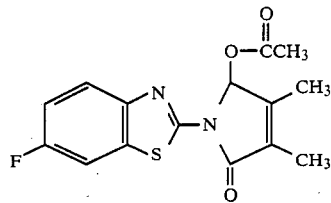
(compound No. 13)

EXAMPLE 2

N-(6-fluoro-2-benzothiazolyl)-3,4-dimethyl-2-hydroxy-5-oxo-2,5-dihydropyrrole (1.39 g) was added to tetrahydrofuran (30 ml) and sodium hydride (0.18 g) at room temperature. The mixture was refluxed for 15 minutes, and then cooled to room temperature. A solution of acetyl chloride (0.79 g) in tetrahydrofuran (10 ml) was added dropwise. After the mixture was refluxed for 3 hours, the solvent was evaporated. The residue was mixed with water, and extracted with chloroform. The chloroform extract was dried over anhydrous magnesium sulfate, and evaporated to dryness under reduced pressure. The solid residue was washed with a small amount of diethyl ether to give the desired N-(6-fluoro-2-benzothiazolyl)-2-oxo-3,4-dimethyl-5-acetyloxy-2,5-dihydropyrrole (1.42 g). m.p. 180°–183° C.

Table 1 below summarizes compounds of formula (I) in accordance with this invention which can be produced by methods similar to the above examples together with the compounds obtained in Examples 1 and 2.

TABLE 1

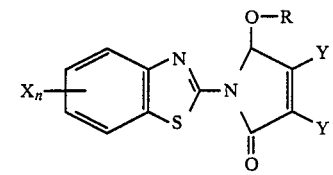

| Comp. No. | R | X | n | Y | m.p. (°C.) |
|---|---|---|---|---|---|
| 1 | H | — | 0 | —CH$_3$ | 183~184 |
| 2 | H | 6-F | 1 | —CH$_3$ | 215~216 |
| 3 | H | 6-Cl | 1 | —CH$_3$ | 221~223 |
| 4 | H | 6-OCF$_3$ | 1 | —CH$_3$ | 228~231 |
| 5 | H | 6-OCHF$_2$ | 1 | —CH$_3$ | 203~206 |
| 6 | H | 6-OCF$_2$CHF$_2$ | 1 | —CH$_3$ | 195~197 |
| 7 | H | 6-C$_6$H$_5$ | 1 | —CH$_3$ | 178~180 |
| 8 | H | 6-C$_3$H$_7$—iso | 1 | —CH$_3$ | 133~135 |
| 9 | H | 6-CH$_3$ | 1 | —CH$_3$ | 203~205 |
| 10 | H | 5-CF$_3$ | 1 | —CH$_3$ | 220~223 |
| 11 | H | 7-Cl | 1 | —CH$_3$ | 228~231 |
| 12 | H | 5,7-Cl$_2$ | 2 | —CH$_3$ | 196~198 |
| 13 | —C(O)—CH$_3$ | 6-F | 1 | —CH$_3$ | 180~183 |
| 14 | H | 5-Cl | 1 | —CH$_3$ | 178~181 |
| 15 | H | 6-F | 1 | —C$_2$H$_5$ | 95 |
| 16 | H | 5-F | 1 | —CH$_3$ | 212~213 |

EXAMPLE 3

Synthesis of a starting material:

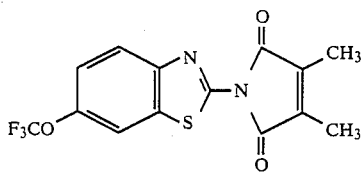

A 100 ml flask was charged with 2-amino-6-trifluoromethoxybenzothiazole (7.03 g), 2,3-dimethylmaleic anhydride (4.16 g) and diphenyl ether (50 ml), and a Dean-Stark separator was attached to the flask. The reaction materials were refluxed for about 5 minutes. After allowing the reaction mixture to cool, it was poured into hexane (200 ml). The resulting crystals were collected by filtration and washed with a small amount of diethyl ether to give N-(6-trifluoromethoxy-2-benzothiazolyl)-dimethymaleimide (7.66 g). m.p. 196°–198° C.

EXAMPLE 4

Synthesis of a starting material by an alternative method:

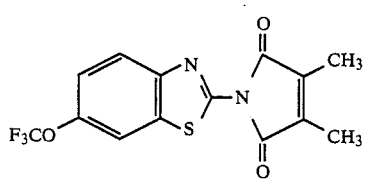

By operating in the same way as in Example 3 using 2-amino-6-trifluoromethoxybenzothiazole (2.34 g), maleic anhydride (2.35 g) and diphenyl ether (30 ml), the same compound (1.87 g) as obtained in Example 3 was formed. m.p. 196°–198° C.

Biological tests:
Comparative compounds

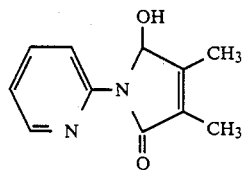 E-1

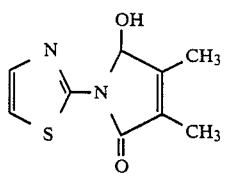 E-2

E-1 and E-2 are compounds described in Japanese Laid-Open Patent Publication No. 23,965/1978.

EXAMPLE 5

Test on weeds in a flooded paddy by water surface application:

Preparation of an acitve compound formulation

Carrier: 5 parts by weight of acetone

Emulsifier: 1 part by weight of benzyloxy polyglycol ether

A formulation of an active compound was obtained as an emulsifiable concentrate by mixing 1 part by weight of the active compound with the above-mentioned amounts of the carrier and the emulsifying agent. A predetermined amount of e formulation was diluted with water.

Testing method

Paddy soil was filled in pots (1/2,000 are; 25×20×9 cm), and rice seedlings (variety: "nihonbare") in the 2.5-leaf stage (15 cm tall) were transplanted at two places per pot each as a stock of three seedlings. Seeds of barnyard grass (*Echinochloa oryzicola* Vasing.), monochoria (*Monochoria vagainalis*, and annual broad-leaved weeds [false pimpernel (*Lindernia pyxidaria* L.), *Rotala indica*, American waterwort (*Elatine triandra*), red stem (*Ammannia multiflora* Roxburgh) and *Dopatrium junceum* Hamilton] were sown and the pots were maintained wet. Two days later, the pots were flooded to a depth of about 2 to 3 cm. Five days after the transplantation of the seedlings, the compound of this invention, in the form of an emulsifiable concentrate as prepared above, was applied to the water surface by a pipette in a predetermined amount. Thereafter, a flooded condition of about 3 cm was maintained, and four weeks after the chemical treatment, the herbicidal effect and the phytotoxicity to rice were evaluated and rated on a scale of 0 to 5 as follows:

Herbicidal effect (evaluated by a weed killing ratio based on a non-treated lot):
5: at least 95% (withered)
4: at least 80% but less than 95%
3: at least 50% but less than 80%
2: at least 30% but less than 50%
1: at least 10% but less than 30%
0: less than 10% (no effect)

Phytotoxicity to rice (evaluated based on a non-treated lot):
5: at least 90% (fatal injury)
4: at least 50% but less than 90%
3: at least 30% but less than 50%
2: at least 10% but less than 30%
1: more than 0 but less than 10%
0: 0% (no phytotoxicity)

The test results are shown in Table 2 by typical examples.

TABLE 2

| Compound No. | Amount of the active component (kg/ha) | Herbicidal effect | | | Phytotoxicity Rice |
|---|---|---|---|---|---|
| | | Barnyard grass | Monochoria | Broad-leaved weeds | |
| 1 | 2 | 5 | 5 | 5 | 0 |
| | 1 | 5 | 5 | 5 | 0 |
| 2 | 2 | 5 | 5 | 5 | 0 |
| | 1 | 5 | 5 | 5 | 0 |
| 4 | 2 | 4 | 5 | 5 | 0 |
| 8 | 2 | 4 | 5 | 5 | 0 |
| 10 | 2 | 4 | 5 | 5 | 0 |
| Comparison | | | | | |
| E-1 | 2 | 2 | 3 | 3 | 2 |
| E-2 | 2 | 3 | 3 | 4 | 5 |

EXAMPLE 6

Test on upland weeds by soil treatment before emergence:-In a greenhouse, rice and corn were sown in 500 cm² pots filled with upland farm soil, and soil containing seeds of livid amaranth (*Amaranthus lividus* L.) and goosefoot (*Chenopodium album* L.) was put over the soil in the pots in a depth of 1 cm.

One day after the sowing, a test chemical in a predetermined concentration, prepared as in Example 5, was uniformly sprayed over the surface layer of the soil in each of the test pots.

Four weeks after the spraying, the herbicidal effect and the phytotoxicity to crops were examined on the same standards as in Example 5. The results are shown in Table 3 by typical examples.

TABLE 3

| Compound No. | Amount of the active component (kg/ha) | Herbicidal effect | | Phytotoxicity | |
|---|---|---|---|---|---|
| | | Livid amaranth | Goose-foot | Rice | Corn |
| 4 | 2 | 5 | 5 | 0 | 0 |
| | 1 | 5 | 5 | 0 | 0 |
| 10 | 2 | 5 | 5 | 1 | 0 |
| | 1 | 5 | 5 | 0 | 0 |
| Comparison | | | | | |
| E-1 | 2 | 2 | 3 | 2 | 1 |
| | 1 | 1 | 1 | 1 | 0 |
| E-2 | 2 | 3 | 3 | 3 | 2 |
| | 1 | 1 | 2 | 2 | 1 |

EXAMPLE 7

Test on upland farm weeds by foliar treatment

In a greenhouse, rice and corn were sown in 500 cm² pots filled with upland farm soil, and soil containing seeds of livid amaranth (*Amaranthus livides* L.) and goosefoot (*Chenopodium album* L.) was put over the soil in the pots in a depth of 1 cm.

After sowing, the plants were grown for 14 days and a test chemical in a predetermined concentration, prepared as in Example 5, was uniformly sprayed onto the test plants in the test pots.

Four weeks after the spraying, the herbicidal effect and the phytotoxicity to crops were examined with the same standards as in Example 5. The results are shown in Table 4 by typical examples.

TABLE 4

| Compound No. | Amount of the active component (kg/ha) | Herbicidal effect | | Phytotoxicity | |
|---|---|---|---|---|---|
| | | Livid amaranth | Goose foot | Rice | Corn |
| 2 | 1 | 5 | 5 | 2 | 1 |
| | 0.5 | 5 | 5 | 0 | 0 |
| 4 | 1 | 5 | 5 | 0 | 0 |
| | 0.5 | 4 | 5 | 0 | 0 |
| 8 | 1 | 5 | 5 | 0 | 0 |
| | 0.5 | 5 | 5 | 0 | 0 |
| 10 | 1 | 5 | 5 | 0 | 0 |
| | 0.5 | 5 | 5 | 0 | 0 |
| Comparison | | | | | |
| E-1 | 1 | 3 | 3 | 3 | 3 |
| | 0.5 | 1 | 2 | 2 | 1 |
| E-2 | 1 | 4 | 4 | 4 | 4 |
| | 0.5 | 3 | 3 | 3 | 2 |

It is understood that the specification and examples are illustrative but not limitative of the present invention and that other embodiments within the spirit and scope of the invention will suggest themselves to those skilled in the art.

We claim:

1. An N-benzothiazolyl-2,5-dihydropyrrole of the formula

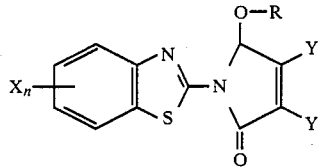

R is hydrogen or an acetyl group,
X is a halogen atom ; an alkyl group, a haloalkyl group or a haloalkoxy group having 1 to 3 carbon atoms; or a phenyl group,
n is 0, 1 or 2, and
Y is methyl or ethyl.

2. A compound according to claim 1, in which
R is hydrogen or an acetyl group,
X is fluorine, chlorine, bromine, an alkyl group having 1 to 3 carbon atoms, a fluoro-substituted alkyl group having 1 to 3 carbon atoms, a fluoro-substituted alkoxy group having 1 to 3 carbon atoms, or a phenyl group, and
Y is methyl or ethyl.

3. A compound according to claim 1, in which
R is hydrogen,
X is fluorine, chlorine, methyl, ethyl, n-propyl, iso-propyl, trifluoromethyl, difluoromethoxy, trifluoromethoxy or tetrafluoroethoxy and
Y is methyl or ethyl.

4. A compound according to claim 1, wherein such compound is N-(2-benzothiazolyl)-3,4-dimethyl-2-hydroxy-5-oxo-2,5-dihydropyrrole of the formula

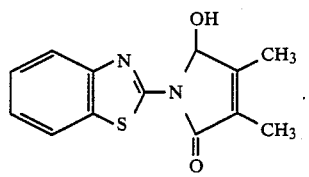

5. A compound according to claim 1, wherein such compound is N-(6-fluoro-2-benzothiazolyl)-3,4-dimethyl-2-hydroxy-5-oxo-2,5-dihydropyrrole of the formula

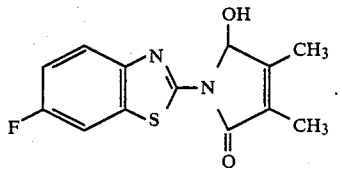

6. A compound according to claim 1, wherein such compound is N-(6-trifluoromethoxy-2-benzothiazolyl)-3,4-dimethyl-2-hydroxy-5-oxo-2,5-dihydropyrrole of the formula

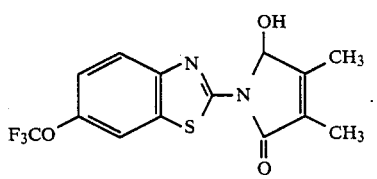

7. A compound according to claim 1, wherein such compound is N-(6-isopropyl-2-benzothiazolyl)-3,4-dimethyl-2-hydroxy-5-oxo-2,5-dihydropyrrole of the formula

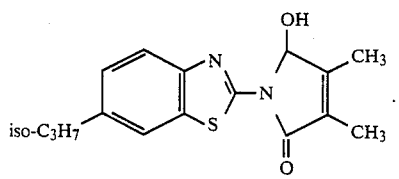

8. A compound according to claim 1, wherein such compound is N-(5-trifluoromethyl-2-benzothiazolyl)-3,4-dimethyl-2-hydroxy-5-oxo-2,5-dihydropyrrole of the formula

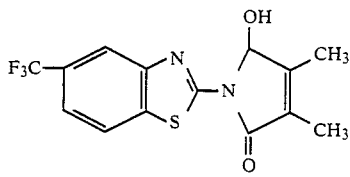

9. A herbicidal composition comprising a herbicidally effective amount of a compound according to claim 1 and a diluent.

10. A method of combating unwanted vegetation which comprises applying to such vegetation or to a habitat thereof a herbicidally effective amount of a compound according to claim 1.

11. The method according to claim 10, wherein such compound is
N-(2-benzothiazolyl)-3,4-dimethyl-2-hydroxy-5-oxo-2,5-dihydropyrrole,
N-(6-fluoro-2-benzothiazolyl)-3,4-dimethyl-2-hydroxy-5-oxo-2,5-dihydropyrrole,
N-(6-trifluoromethoxy-2-benzothiazolyl)-3,4-dimethyl-2-hydroxy-5-oxo-2,5-dihydropyrrole,
N-(6-isopropyl-2-benzothiazolyl)-3,4-dimethyl-2-hydroxy-5-oxo-2,5-dihydropyrrole or
N-(5-trifluoromethyl-2-benzothiazolyl)-3,4-dimethyl-2-hydroxy-5-oxo-2,5-dihydropyrrole.

* * * * *